(12) United States Patent
Arnott

(10) Patent No.: US 7,144,378 B2
(45) Date of Patent: Dec. 5, 2006

(54) QUICK-RELEASE TORQUER APPARATUS FOR DELIVERING AND MAINTAINING A MEDICAL GUIDEWARE

(76) Inventor: Richard J. Arnott, 113 Hodil Ter., Pittsburgh, PA (US) 15238

( * ) Notice: Subject to any disclaimer, the term of this patent is extended or adjusted under 35 U.S.C. 154(b) by 440 days.

(21) Appl. No.: 10/698,835

(22) Filed: Oct. 31, 2003

(65) Prior Publication Data

US 2005/0096566 A1    May 5, 2005

(51) Int. Cl.
| | |
|---|---|
| A61B 5/00 | (2006.01) |
| A61M 25/00 | (2006.01) |
| A61M 1/00 | (2006.01) |
| A61M 31/00 | (2006.01) |
| A61M 37/00 | (2006.01) |
| A61M 5/178 | (2006.01) |
| A61B 17/56 | (2006.01) |
| A61B 17/00 | (2006.01) |
| A61B 4/00 | (2006.01) |
| A61B 17/58 | (2006.01) |
| A61B 17/60 | (2006.01) |
| A61F 5/04 | (2006.01) |
| A61F 11/00 | (2006.01) |

(52) U.S. Cl. ................ 600/585; 604/264; 604/27; 604/93.01; 604/95.03; 604/95.04; 604/164.01; 604/164.13; 604/528; 604/523; 606/53; 606/54; 606/99; 606/129; 606/103; 606/108

(58) Field of Classification Search ............. 600/585; 606/53, 54, 99, 103, 108, 129; 604/264, 604/27, 93.01, 95.03, 95.04, 164.01, 164.13, 604/528, 523
See application file for complete search history.

(56) References Cited

U.S. PATENT DOCUMENTS

| | | | |
|---|---|---|---|
| 4,873,978 A | 10/1989 | Ginsburg | |
| 5,161,534 A | 11/1992 | Berthiaume | |
| D333,182 S * | 2/1993 | Yoshikawa | ............... D24/133 |
| 5,312,338 A | 5/1994 | Nelson et al. | |
| 5,325,746 A | 7/1994 | Anderson | |
| 5,325,868 A | 7/1994 | Kimmelstiel | |
| 5,579,780 A | 12/1996 | Zadini et al. | |
| 5,606,980 A | 3/1997 | Calhoun et al. | |
| 5,634,475 A | 6/1997 | Wolvek | |
| 6,030,349 A | 2/2000 | Wilson et al. | |
| 2002/0072730 A1* | 6/2002 | McGill et al. | .............. 604/525 |
| 2003/0229297 A1* | 12/2003 | Christensen et al. | ........ 600/585 |

* cited by examiner

*Primary Examiner*—Max F. Hindenburg
*Assistant Examiner*—Jeffrey Hoekstra
(74) *Attorney, Agent, or Firm*—McKay & Associates

(57) ABSTRACT

The present invention provides a torquer for maneuvering a medical guidewire during endovascular surgical procedures or the like, which can be easily positioned and re-positioned along the length of the wire. A clamp-like device is formed with a top arm and a bottom arm connected to one another by means of a flap hinge. A horizontal slit is defined within the flap hinge, and a vertical slit is defined on a clamping tongue positioned at the top distal end of the top arm, such that the torquer is placed onto the guidewire and snapped into place with the guidewire penetrating the vertical slit. A wire channel means is further defined between the two arms to hold the guidewire within the torquer.

12 Claims, 4 Drawing Sheets

QUICK-RELEASE TORQUER APPARATUS FOR DELIVERING AND MAINTAINING A MEDICAL GUIDEWARE

BACKGROUND

1. Field of the Invention

The present invention is directed to a method and apparatus for delivering, manipulating and repositioning a guidewire to and beyond an operative site in any of a variety of medical procedures employed to treat any number of medical conditions in human and/or animal patients.

2. Description of the Related Art

In many medical procedures, endovascular devices are delivered during diagnostic and surgical procedures, and it is useful and/or necessary to deliver these devices on or over a medical guidewire.

Minimally invasive interventional medical diagnosis procedures in general, and minimally invasive endovascular therapy in particular, are medical events where devices are delivered over a guidewire during the procedure, and each has enjoyed unprecedented expansion to treat patients because of the numerous medical benefits associated with not having to enter the body through more invasive surgical techniques. These benefits include, but are not limited to, less trauma and/or scarring for patients, less time to heal, less risk of infection and decreased length of hospital stays, to name but a few.

More particularly, minimally invasive endovascular therapy is often used to treat diseased vessels, e.g., arteries and veins. With such therapy, small instruments are inserted into the vessels through a puncture or access opening made in one of the vessels at an entry site and are advanced through the circulatory system to an operative site where the vessel has become diseased. There, the instruments are used to diagnose and/or repair the diseased or operative site. Typically, the goal of such therapy is to identify and and treat by dilation full or partial blockages of the diseased vessel. Such blockages may have developed over time or may have developed quickly, as for example, in response to an injury. One common source of such blockage is thromboemboli which has formed in the vessel. Thrombus is an aggregation of platelets, fibrin, clotting factors and cellular components of blood that spontaneously form and attach on the interior wall of a vein or artery. Thromboemboli are emboli of thrombus which operate to partially or completely occlude the interior or lumen of the blood or other vessel.

Techniques to open and/or maintain the dilation of the partially or completely occluded lumen of blood or other vessels include balloon angioplasty and stenting. Balloon angioplasty is the delivering of a balloon over a guidewire and positioning it in an obstruction or partially occluded section of the vessel, inflating the balloon to compress the build up. Stenting is the temporary or permanent inserting, again over a guidewire, of a tube-like support within the vessels to keep the vessel open.

Minimally invasive endovascular diagnosis and therapy has the significant advantages of being less invasive than traditional surgical techniques and causing less trauma to the patient. However, these procedures are also inherently more complicated: they may inadvertently puncture the vessel wall or dislodge and free particles or objects during the procedures as discussed above. Particularly, this complication results from the small clearances between instruments and the interior of the vessels of the body, and reaching the operative site with the tools is very difficult (due to the considerable branching of the circulatory system that may occur between the entry site into the blood vessel and the operative site). Endovascular diagnosis and therapy is further complicated by the fact that the entry site is often far from the operative site, as for example, where the entry site is in the thigh at the femoral artery and the operative site is located in the neck at the carotid artery. Even when the surgeon's instruments have been properly advanced to the operative site, manipulating the tools to perform their respective functions at the operative site is often difficult for the surgeon due to many factors including guidewire movement, the close quarters at the operative site and the distance between the entry site and the operative site.

One method and apparatus commonly used by surgeons to ensure the tools reach the operative site is to first thread a simple guidewire to or beyond the operative site. Thereafter, various tools are threaded over the guidewire by the surgeon to reach the operative site. It is an important aspect of such guidewires that they must be easy to manipulate within the vessels, including, in certain cases, through lesions or areas of blockage in the vessel by the surgeon. In addition to exhibiting sufficient resiliency so as to be pushable in the vessel, the guidewire must exhibit sufficient flexibility and maneuverability to enable the surgeon to traverse the many twists and turns of the circulatory (or other) system to reach the operative site.

Two major aspects which influence the ability of a surgeon to manipulate the guidewire through the circulatory or other system are the guidewire's advancement and "torquability". As defined herein, "torquability" is a qualitative measure of the surgeon's ability to rotate the proximal region of the guidewire that extends outside of the patient's body during the advancement of the guidewire to the operative site and translate that rotation to the distal end of the guidewire. It is this rotation at the proximal region of the guidewire, when mechanically transmitted to the distal end of the guidewire, which advances the distal end through the patient's blood or other vessels to the operative site. A lack of correlation between rotation at the proximal region of the guidewire and rotation at the distal end of the guidewire is referred to as reduced torquability and is undesirable. A high degree of correlation is referred to as a high degree of torquability and is desirable. As may be appreciated, it is most desirable for the guidewire to have an exact correlation or high torquability between the rotation applied proximally at the proximal region of the guidewire and the rotation developed distally in the guidewire, so that the surgeon can carefully control, advance, and direct the medical guidewire. With known devices, there is considerable difference between the amount of rotation applied at the proximal region of the guidewire and the amount of rotation developed at the distal end of the guidewire, making it very difficult for surgeons to maneuver the distal end of the guidewire.

Even where the guidewire exhibits the desired torquability characteristics, and the tools have been properly threaded to the operative site and have been properly manipulated to perform their respective functions at the operative site, there remains the problem noted above, namely, that the process of dilating the occlusion and/or inserting the stent may dislodge or free small particles or objects, also known, among other things, as clots, fragments, plaque, emboli, thromboemboli, etc. More particularly, with respect to endovascular therapy, the term "embolic event" has come to be used to describe complications where thrombus or plaque is shed inadvertently from a lesion to migrate to smaller vessels beyond the operative site to create a full or partial occlusion of the lumen of the vessel or vessels. This is most undesirable and can lead to many complications. These complications are dependent upon the site in the body where such emboli become lodged, downstream of the operative site. They include stroke, myocardial infarction, kidney failure, limb loss or even death. With increasing emphasis, surgeons state the need to reduce the likelihood of complications such that assurance against embolic events will become the typical result of endovascular therapy.

During the previously described procedures, it is necessary to remove tools, devices and catheters from a patient via a guidewire while the guidewire itself remains in the patient. Typically during a procedure, a torquer is placed on and removed from a guidewire each time a new device is utilized. This necessitates the complete removal of the torquer from the guidewire by sliding the torquer to the proximal end of the guidewire. The guidewire being of considerable length, relates to several awkward motions which again can cause damage to the intima of the vessel. The torquer is also advanced several times along the guidewire with the use of each new tool. With most torquers, this requires a two-handed action to loosen, slide and then retighten the torquer before the next step in the procedure can be made, this is time consuming and costly to both the physician and patient.

Devices are seen in the art that assist in the manipulation of the guidewire external to the surgical opening, such that the internally displaced distal end of the guidewire may be maneuvered through the vessel as a result of movement from the guidewire's proximal end.

U.S. Pat. No. 6,030,349 to Wilson et al. teaches a medical guidewire torquer comprising a single cylindrical body having a groove displaced therein for receiving the wire, wherein an amount of pressure may be applied to the medical guidewire so movement and immobilization of the torquer along the proximal end may be performed.

U.S. Pat. No. 5,325,868 to Kimmelstiel shows a self-gripping medical wire torquer which includes a single sleeve body having a clamping device and a release mechanism for temporarily releasing the clamp means to slide and reposition the torquer along the wire.

Other devices for manipulating a medical guidewire are known in the art, but these and the above devices suffer generally, not only because of the above reasons for lack of torquability, but because of cost considerations and their inherent complexity. Because of concerns for sterility, and the need for ease of use, a surgeon will typically dispose of torquer devices regularly during different stages of the advancement of the guidewire, even for the same patient. Surgeons have found that it is more expedient to have many disposable torquer devices available than to repeatedly reposition and keep track of a single torquer. For this reason, simplicity of design and the ease of use by one-hand manipulation is of utmost importance.

There is need then in the art for a torquer device to maximize torquability, which is simple in design, easy to mount on, slide upon, and remove from the medical guidewire, using a single-hand clamping technique.

SUMMARY OF THE INVENTION

It is an objective of the present invention to provide a torquer for a medical guidewire that may be mounted, repositioned, and removed using a single-hand release and fastening means.

It is further an objective of the present invention to provide a torquer having a means to facilitate the manipulation and maneuverability of the guidewire.

It is further an objective of the present invention to provide a torquer having a grip surface positioned on the top and/or bottom surface thereof to further assist in the manipulation and maneuverability of the guidewire.

It is further an objective of the present invention to provide a torquer having an efficient means for removably positioning the torquer along the length of the guidewire.

It is further an objective of the present invention to provide a torquer of one-piece design, thereby facilitating the manufacture and disposability thereof.

Accordingly, the above and other objectives are met by providing a torquer for maneuvering a guidewire, comprising a top arm having a top distal end and a top proximal end; a clamping tongue disposed downwardly from the top distal end; a bottom arm having a bottom distal end and a bottom proximal end, the bottom proximal end flexibly connected to the top proximal end by means of a flap hinge; a proximal slit defined horizontally between the bottom proximal end and the top proximal end; and a distal slit defined vertically within the clamping tongue, wherein each slit is adapted to receive the medical guidewire, thereby enabling the guidewire to be maneuvered by the torquer when the torquer is clamped shut.

The present invention then will open and close in a clamping manner. In its closed position the clamping tongue will be clipped onto a bottom lip abutting the bottom distal end of the bottom arm as the wire is positioned within each slit. The wire may further be situated within a wire channel means defined on the surfaces of the bottom and top arm when the arms are closed, thereby keeping the torquer in a removably fixed position and the particular portion of the guidewire enveloped by the torquer in a stable position. This will result in the ability of the user to manipulate and/or maneuver the guidewire from the point at which the torquer is attached.

In its open position, the torquer may simply be pulled away from the guidewire (as opposed to being slid off the end of the guidewire, thus allowing for a rapid exchange of tools and/or devices), or the guidewire can remain within the proximal slit and/or the distal slit, thus allowing the torquer to slide and travel along the length of the guidewire and simply be repositioned along the guidewire at an alternative point by clamping and snapping the two arms together.

DETAILED DESCRIPTION OF THE PREFERRED EMBODIMENT

The invention will now be described in detail in relation to a preferred embodiment and implementation thereof which is exemplary in nature and descriptively specific as disclosed. As is customary, it will be understood that no limitation of the scope of the invention is thereby intended. The invention encompasses such alterations and further modifications in the illustrated method, and such further applications of the principles of the invention illustrated herein, as would normally occur to persons skilled in the art to which the invention relates.

Figure 1:
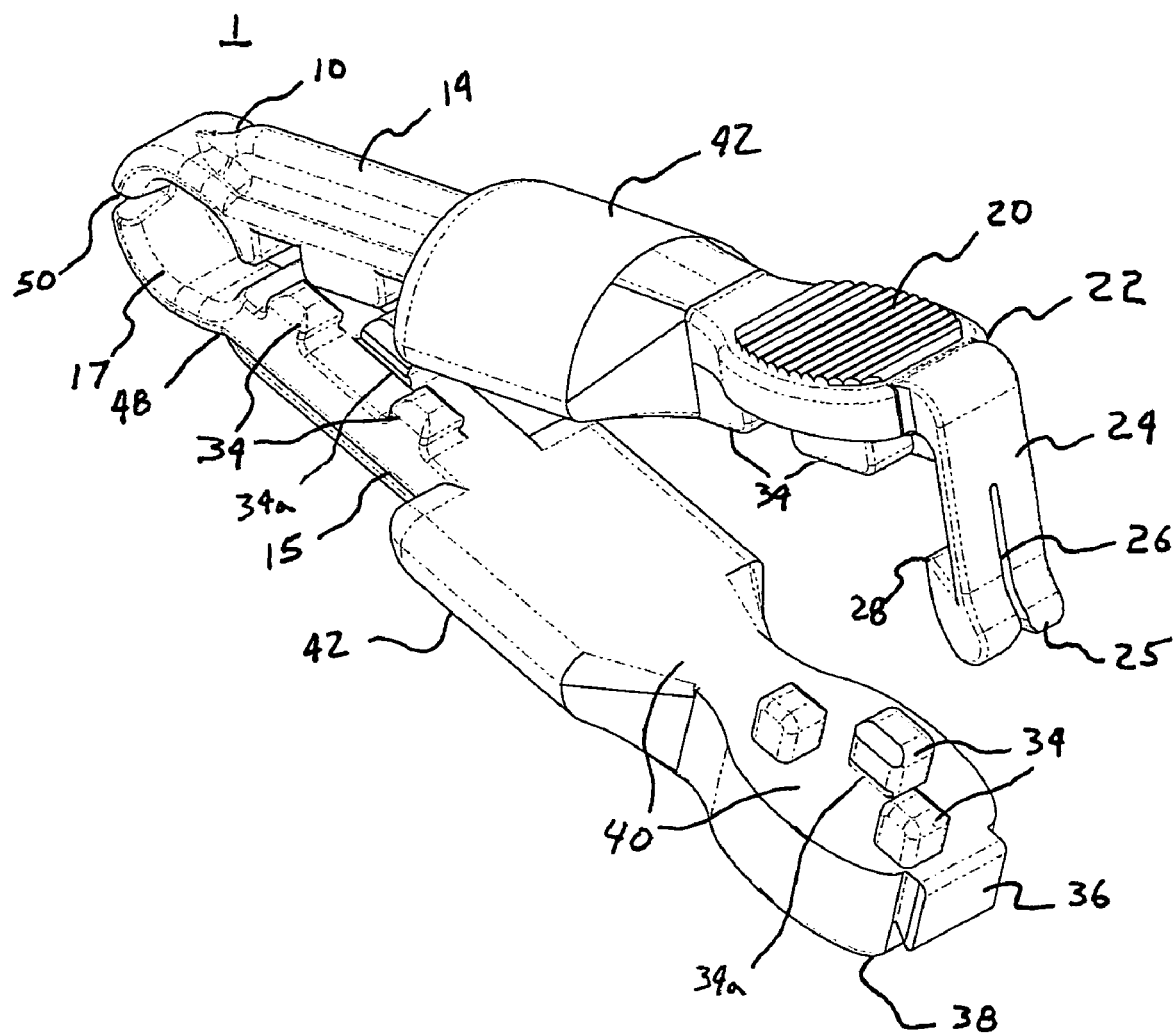
FIG. 1 is a perspective view of the torquer in an open position.
Figure 1A:
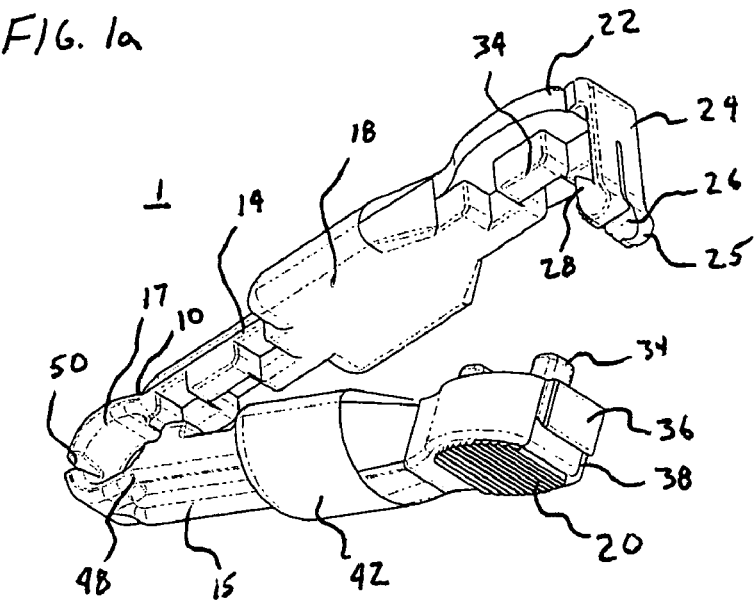
FIG. 1a is a rotated perspective view of the torquer in in an open position.
Figure 2:
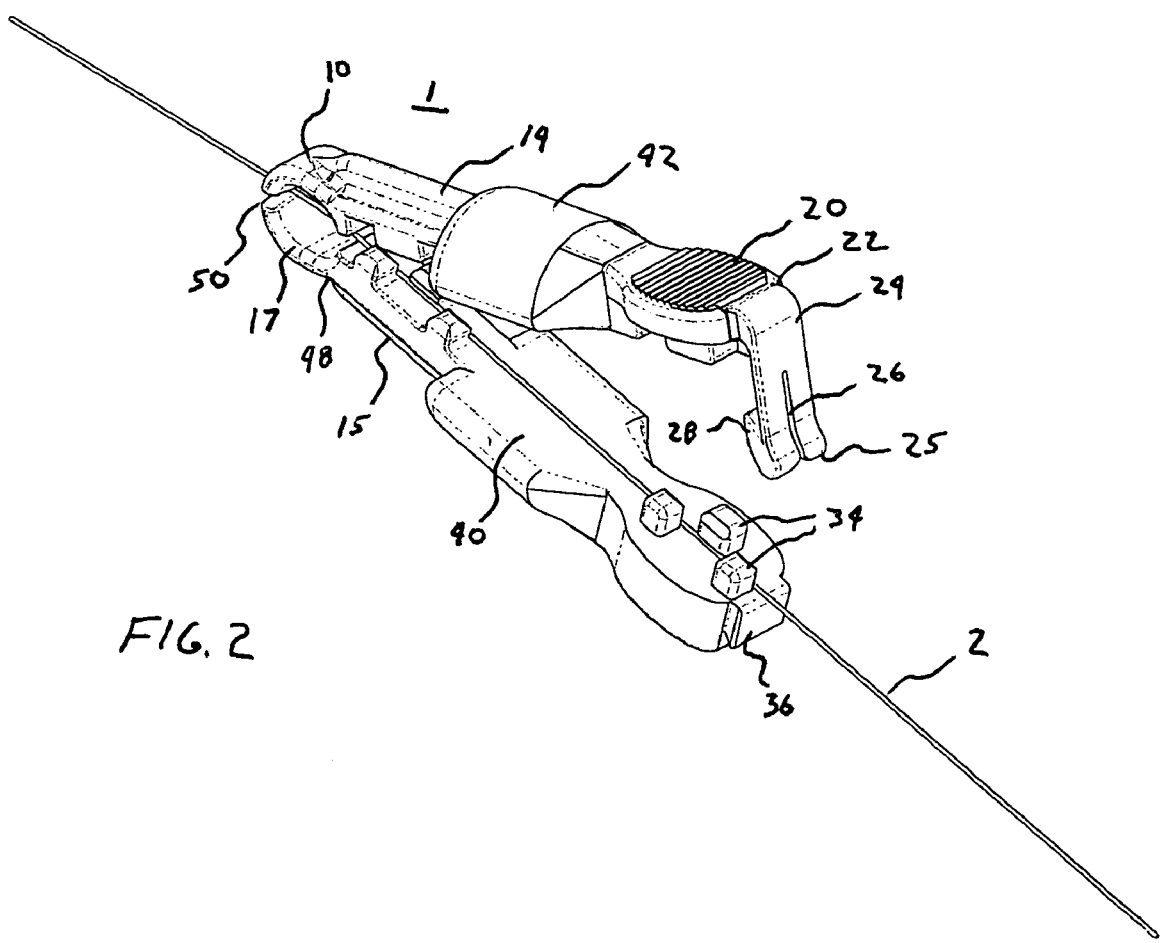
FIG. 2 is a perspective view of the torquer in an open position showing the location of the medical guidewire.
Figure 3:
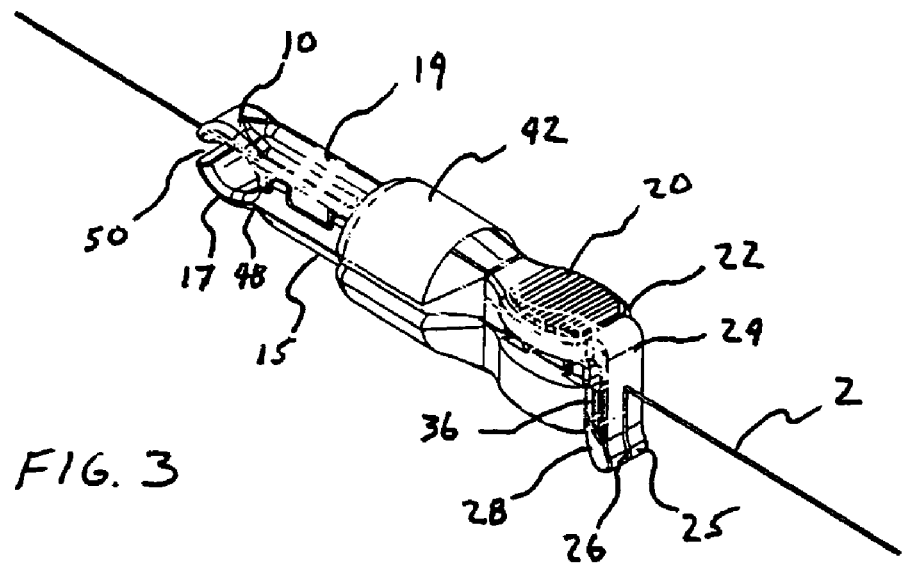
FIG. 3 is a perspective view of the torquer in a closed position showing the medical guidewire positioned therein.
Figure 4:
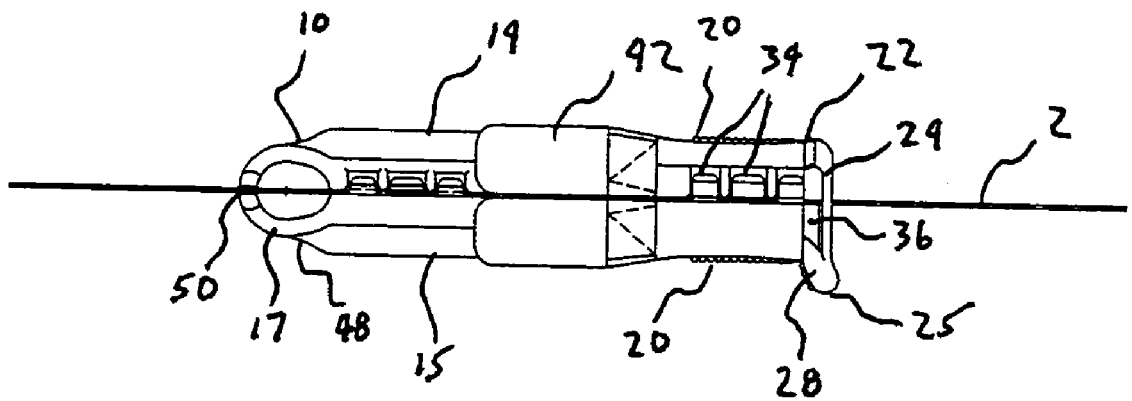
FIG. 4 is a side view of the torquer in a closed position with the guidewire positioned therein.
Figure 5:
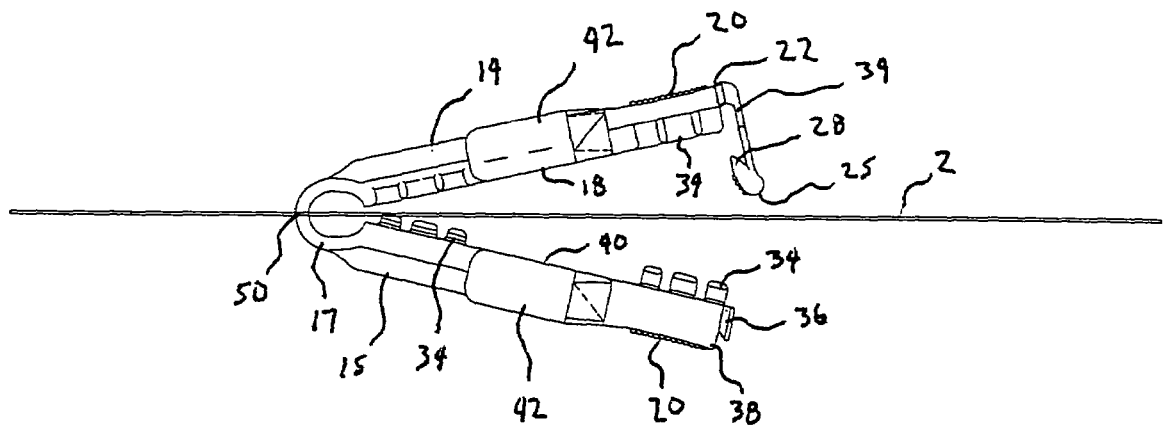
FIG. 5 is a side view of the torquer in an open position showing the guidewire positioned within the flap hinge.
Figure 6:
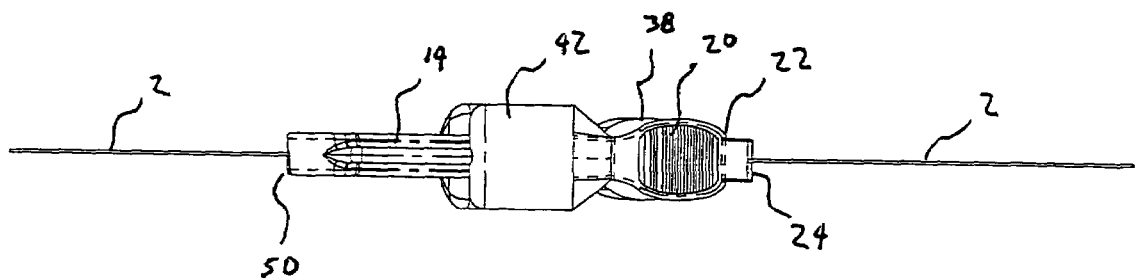
FIG. 6 is a top view of the torquer with the guidewire positioned therein.

FIGS. 1–6 demonstrate the present invention in the form of a torquer 1 configured to be positioned on a guidewire 2. In the preferred embodiment, the guidewire 2 suited for use with the present invention is a medical guidewire 2, wherein the torquer 1 is positioned on or fastened to the portion of the medical guidewire 2 external to the patient, such that the medical guidewire 2 is then capable of being manipulated or maneuvered through a blood vessel or other tract by a surgeon. The guidewire 2 is typically in the range of 0.011 inches—0.040 inches in diameter, typically 0.014 inches in diameter. As should be understood, the dimensions of any wire-receiving portions manufactured for the torquer 1 may vary according to the dimensional specifications of the guidewire 2.

The torquer is generally comprised of a top arm 14 and a bottom arm 15. The top arm 14 is hingedly attached to the bottom arm 15 in a way that enables the two arms to function in a clamping manner. Though any type of hinge may be used, in the preferred embodiment, the torquer 1 is a one-piece mold design of rubber or plastic or the like wherein the top arm 14 is attached to the bottom arm by means of an integral, flexible flap hinge 17. Specifically, the top arm 14 has a top distal end 22 and a top proximal end 10 relative to the flap hinge 17 of the two arms. The bottom arm 15 has a bottom distal end 38 and a bottom proximal end 48. Thus, the bottom proximal end 48 is flexibly connected to the top proximal end 10 to form the flap hinge 17.

A clamping tongue 24 is attached or integrally formed and downwardly disposed from the top distal end 22. Defined within the clamping tongue 24 is a generally vertical distal slit 26. In the preferred embodiment, the distal slit 26 is defined medially within and along the length of the clamping tongue 24. The distal slit 26 is appropriately sized/defined with a width which allows the guidewire 2 to fit therein.

As a preferred means for clamping the top arm 14 to the bottom arm 15, a tongue clip 28 is provided on the tip 25 of the clamping tongue 24. The tongue clip 28 is formed on the tip 25 and projects slightly upward and inward therefrom. The tongue clip 28 is configured to snap onto a bottom lip 36 integrally formed on the bottom distal end 38 of the bottom arm 15. The bottom lip 36 may be any type of abutment formed of a suitable shape to allow the clamping tongue 24 to fasten to the bottom arm 15. Thus, the top arm 14 with the distal slit 26 is configured to clamp and snap down onto the bottom arm 15. To open the torquer 1, the clamping tongue 24 is simply pushed away from the bottom lip 36 to disengage the tongue clip 28 from the bottom lip 36.

Furthermore, a proximal slit 50 is horizontally defined within the flap hinge 17. Similar to the vertical distal slit 26, the proximal slit 50 is sized/defined to allow the guidewire 2 to fit therein. Preferably, the horizontal length of the proximal slit 50 is one-half the width of the flap hinge 17 so that the guidewire 2 can be positioned medially within the torquer 1. Thus, in operation, the torquer 1 is fastened to the guidewire 2 by aligning and sliding the proximal slit 50 onto the guidewire 2 with the torquer 1 in an open position (see FIG. 5). The guidewire 2 is then snapped into the two groups of projections 34 (as further described) which entrap the guidewire 2 and allow for easy sliding of the torquer 1. The top arm 14 and bottom arm 15 are then clamped together as the guidewire 2 slides into the distal slit 26 of the clamping tongue 24.

As a preferred embodiment as a means for further securing the torquer 1 on the guidewire 2 and to provide greater torqueability to manipulate the guidewire 2, a wire channel means is provided on at least one of the surfaces with which the guidewire 2 will come into contact when the torquer is clamped shut on the guidewire 2. The bottom arm 15 has a top surface 40. The top arm 14 has an underlying surface 18 aligned with and which opposes the top surface 40 of the bottom arm 15. The wire channel means is formed on either or both of the top surface 40 and underlying surface 18. As shown, multiple and alternating projections 34 are integrally formed on the top surface 40 of the bottom arm 15 positioned near the bottom distal end 38 and in a spaced apart relation to provide a channel in which the guidewire 2 may be positioned. A longitudinal groove 34a or detent is formed on each projection 34 of the bottom arm 15. Each groove 34a further nests the guidewire 2 while allowing the guidewire 2 to rotate freely and move longitudinally within the torquer 1. In an unlocked position, the torquer 1 can advance rapidly along the wire and easily be positioned. The grooves 34a also prevent the torquer 1 from falling off the guidewire in an unlocked position. The guidewire 2 fits into each groove 34a, and a second compression or "snap" of the torquer 1 closes the two arms and "locks" the torquer 1 into a position on the guidewire 2 so that the torquer 1 can rotate and advance the guidewire 2.

Preferably, another group of projections 34 are then situated near the bottom proximal end 48, and also on similar opposing positions on the underlying surface 18 of the top arm 14. The projections 34 on the underlying surface 18 are positioned in an alternating manner which allows them to mate with the underlying projections 34 on the top surface 40 of the bottom arm 15, thereby firmly "locking" the guidewire 2 in place. In a similar fashion, and as should be equivalently understood, the wire channel means may be constructed using these projections 34, but which projections 34 travel the length of the top surface 40 and/or the underlying surface 18. The wire channel means may further be simply a single channel defined on either the underlying surface 18 or top surface 40 by parallel rail members (not shown) adapted to receive the guidewire 2 and having a width similar to the distal slit 26 and/or the proximal slit 50. The underlying surface 18 may further be either flat or ribbed with one or more teeth to allow the arms to mate to one another while securing the guidewire 2.

As a further embodiment, a portion of the top arm 14 and/or the bottom arm 15 may be enlarged to enhance the torqueability of the torquer. As shown, leverage is enhanced by providing a torque assist area 42, which is generally a partially or entirely expanded portion of the top arm 14 and/or the bottom arm 15. A grip of the user may further be enhanced by providing a more frictional or rubber-like grip surface 20 on or near the top distal end 22 and/or the bottom distal end 38.

Thus, the present invention is constructed to give high torqueability between the rotation applied proximally at the proximal region of the guidewire and the rotation developed distally in the guidewire, so that the surgeon can carefully control and direct the medical guidewire 2 and easily position and re-position the torquer 1 along the length of the medical guidewire 2.

I claim:

1. A one-piece, disposable torquer for maneuvering a guidewire, comprising:
   a top arm having a top distal end and a top proximal end;
   a clamping tongue disposed downwardly from said top distal end;
   a bottom arm having a bottom distal end and a bottom proximal end, said bottom proximal end flexibly connected to said top proximal end by means of a flap hinge;
   a proximal slit defined horizontally within half the width of said flap hinge; and,
   a distal slit defined vertically within the length of said clamping tongue, wherein said proximal slit and said distal slit are adapted to receive said guidewire, and wherein said torquer can be removed from said guidewire without having to slide said torquer off an end of said guidewire.

2. The torquer of claim 1, further comprising a wire channel means for positioning said guidewire between said bottom arm and said top arm when said top arm and said bottom arm are clamped together.

3. The torquer of claim 1, further comprising a torque-assist area defined on both said top arm and said bottom arm.

4. The torquer of claim 1, further comprising a grip surface defined on said top arm near said top distal end.

5. The torquer of claim 1, further comprising a grip surface defined on said bottom arm near said bottom distal end.

6. The torquer of claim 1, further comprising a means for releasably clamping said clamping tongue to said bottom distal end.

7. A one-piece, disposable torquer for maneuvering a guidewire, comprising:
   a top arm having an underlying surface;
   a bottom arm hingedly connected to said top arm by means of a flap hinge, said bottom arm having a top surface opposed and aligned with said underlying surface of said top arm; and,
   a wire channel means for positioning said guidewire between said bottom arm and said top arm, said wire channel means integrally formed on at least one of said top surface or said underlying surface, said wire channel means on said top surface further comprising multiple and alternating projections integrally formed thereon in spaced apart relation;
   each said projection having formed thereon a longitudinal groove at a base thereof, whereby said guidewire can be nested while allowing the guidewire to rotate freely and move longitudinally within said torquer when in a unlocked position.

8. The torquer of claim 7, further comprising a proximal slit defined horizontally within said flap hinge.

9. The torquer of claim 7, further comprising a torque-assist area defined on both said top arm and said bottom arm.

10. The torquer of claim 7, further comprising a grip surface defined on said top arm.

11. The torquer of claim 7, further comprising a grip surface defined on said bottom arm.

12. The torquer of claim 7, further comprising a means for releasably clamping said top arm to said bottom arm.

* * * * *